United States Patent [19]

Rosenquist

[11] Patent Number: 4,696,997
[45] Date of Patent: Sep. 29, 1987

[54] CYCLIC CARBONATE OLIGOMER COMPOSITION

[75] Inventor: Niles R. Rosenquist, Evansville, Ind.

[73] Assignee: General Electric Company, Mt. Vernon, Ind.

[21] Appl. No.: 796,984

[22] Filed: Nov. 12, 1985

[51] Int. Cl.⁴ .............................................. C08G 63/62
[52] U.S. Cl. ..................................... 528/271; 524/611;
528/196; 528/370; 528/371; 549/228
[58] Field of Search ................. 549/228; 528/370, 271

[56] References Cited

U.S. PATENT DOCUMENTS 4,568,755  2/1986  Mues et al. ........................ 549/228

Primary Examiner—Harold D. Anderson
Attorney, Agent, or Firm—Martin B. Barancik

[57] ABSTRACT

A composition comprising at least one oligomer of the formula

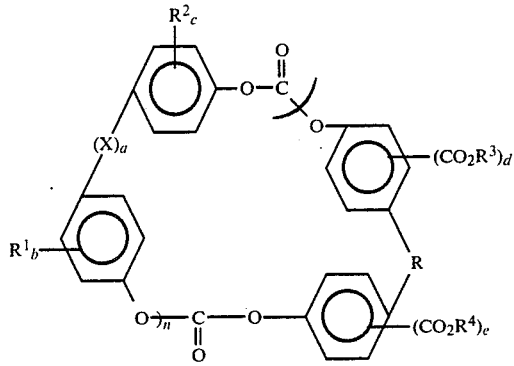

wherein
X is selected from the group consisting of alkylene of two to twelve carbon atoms, inclusive, alkylidene of one to twelve carbon atoms, inclusive, cycloalkylene of four to twelve carbon atoms, inclusive, cycloalkylidene of four to twelve carbon atoms, inclusive, —S—, —O—, —S—S—,

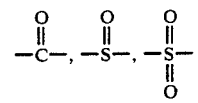

a is zero or 1;
n is an integer of one to about fifteen;
R is alkylene of two to eight carbon atoms, inclusive, or alkylidene of one to eight carbon atoms, inclusive;
$R^1$ and $R^2$ are the same or different and are alkyl or one to four carbon atoms, inclusive or halo;
b and c are the same or different and are an integer of zero to four; and
$R^3$ and $R^4$ are the same or different and are alkyl of one to eight carbon atoms, inclusive, or phenyl; and
d and e are individually integers of 0, 1 or 2 with the proviso that d+e is at least one.

4 Claims, No Drawings

CYCLIC CARBONATE OLIGOMER COMPOSITION

BACKGROUND OF THE INVENTION

Polycarbonates are well known polymers which have good property profiles, particularly with respect to impact resistance, electrical properties, dimensional rigidity and the like. These polymers are generally linear, but can be made with branched sites to enhance their properties in specific ways. Low levels of branching are generally incorporated into the resin by copolymerizing into the polymer backbone a tri or higher functional reagent to yield a thermoplastic polycarbonate resin with enhanced rheological properties and melt strength which make it particularly suitable for such types of polymer processing procedures as the blow molding of large, hollow containers and the extrusion of complex profile forms.

Sufficiently higher levels of branching sites in the resin will cause resin chains to join to each other to form partially or fully crosslinked resin networks which will no longer be thermoplastic in nature and which are expected to exhibit enhancements, over corresponding linear resins, in physical properties and/or in their resistance to abusive conditions, such as exposure to organic solvents and elevated temperatures. A wide variety of means have been employed to produce crosslinking in polycarbonate resin. These generally involve the incorporation of a suitably reactive chemical group either into the resin chain at its time of manufacture or as an additive to the resin after manufacture, or both. These reactive groups and the reactions they undergo are generally dissimilar from those characteristic of polycarbonate resin itself and are therefore prone to have detrimental side effects on the physical and/or chemical properties of the polymer. The conventional test used to judge the success of these means for crosslinking is to observe the formation of gels due to the crosslinked material when a resin sample is mixed with a solvent, such as methylene chloride, in which normal linear polycarbonate resin is highly soluble.

A new method has been discovered to prepare branched or crosslinked polycarbonate resin. This approach involves incorporating a multifunctional comonomer of better than two reactive groups into cyclic bisphenol carbonate oligomers. The thus prepared cyclic oligomers are then reacted at elevated temperature with catalysis to yield high molecular weight polycarbonate resin. Generally the polymerization occurs under melt conditions. This reaction is thought to proceed by a multi-step ring opening addition mechanism. During this polymerization the functional groups of the multifunctional comonomer are available for building branches and/or for crosslinking one polycarbonate chain to another polycarbonate chain.

This new method to prepare branched or crosslinked polycarbonate resin is an improvement over previous methods in that the resin is initially low in molecular weight and thus has low viscosity and is easily processed into its desired forms. It is then converted under convenient reaction conditions to high viscosity branched resin or to crosslinked resin. This is accomplished by incorporating into the resin multifunctional comonomers with chemical groups with similar structure and reactivity to the repeat units of the resin so that the possibility of detrimental side effects on resin properties are minimized.

SUMMARY OF THE INVENTION

In accordance with the invention, there is a composition comprising a structure of the formula:

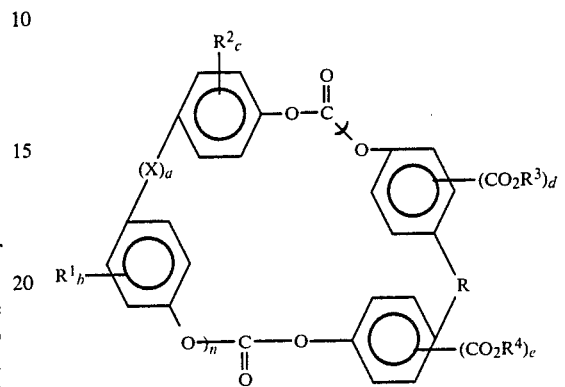

wherein

X is selected from the group consisting of alkylene of two to twelve carbon atoms, inclusive, alkylidene of one to twelve carbon atoms, inclusive, cycloalkylene of four to twelve carbon atoms, inclusive, cycloalkylidene of four to twelve carbon atoms, inclusive, —S—, —O—, —S—S—,

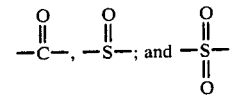

a is zero or 1;

n is an integer of one to about fifteen;

R is alkylene of two to eight carbon atoms, inclusive or alkylidene of one to eight carbon atoms, inclusive;

$R^1$ and $R^2$ are the same or different and are alkyl of one to four carbon atoms, inclusive or halo;

b and c are the same or different and are an integer of zero to four;

$R^3$ and $R^4$ are the same or different and are alkyl of one to eight carbon atoms, inclusive, or phenyl;

d and e are an integer of 0, 1 or 2 with the proviso that the sum of d and e is at least one.

It should be noted that the preponderance of the cyclic oligomers will have only one multifunctional conomoner in the enclosed chain. However, some cyclic oligomers will have more than one multifunctional comononer in the enclosed chain.

In further accordance with the invention, there is a composition comprising cyclic oligomers of Formula I in admixture with cyclic oligomers of the Formula II:

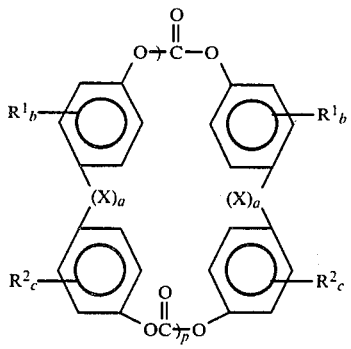

II.

wherein p is an integer from one to about fifteen (15) and X, $R^1$, $R^2$; a, b and c have the same scope as above.

Examples of the preparation and polymerization of cyclic oligomers are described in copending Ser. No. 704,122, filed Feb. 22, 1985 and Ser. No. 723,672, filed Apr. 16, 1985 and refereneces contained therein, all of which are incorporated herein by reference.

A further aspect of the invention is a composition comprising a very high molecular weight aromatic polycarbonate polymer having a branching site from the reaction residue of

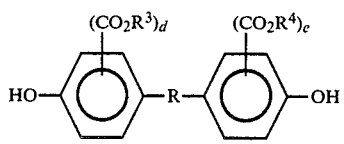

III.

wherein R, $R^3$, $R^4$, d and e are defined with the same scope as in Formula I.

Comonomers of Formula III can be incorporated into linear polycarbonate resins using standard interfacial conditions and then reacted under melt transesterification conditions to provide branched or crosslinked resin. However it is more advantageous to incorporate comonomers III into cyclic oligomers and then to react those oligomers under melt transesterification conditions to provide the branched or crosslinked resin. This is due to the ability with cyclic oligomers to increase the ratio of multifunctional and bifunctional reactive sites to monofunctional reactive sites in a more convenient manner than that employed with interfacial resins. Thus, crosslinking density and extent is more uniform and can be higher. These resins can be used in the preparation of useful articles such as fibrous reinforced material (composites). Such articles can be easily prepared by mixing or impregnating the fiber with the low viscosity cyclic oligomers of this invention followed by thermal conversion to crosslinked polymer. The remainder of the polymer consists at least essentially of residues of the dihydric phenol

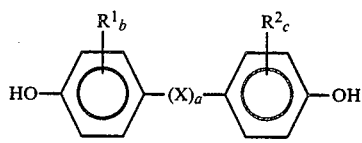

IV.

where X, $R^1$, $R^2$, a, b and c are previously defined in Formula I.

DESCRIPTION OF THE INVENTION

The incorporation of the compound(s) of Formula III into a cyclic oligomeric structure is done under standard cyclics producing reaction conditions. The cyclic oligomers are mixtures generally having degrees of polymerization of from about 2 to about 15. Those compositions have relatively low melting points as compared to single compounds such as the corresponding cyclic trimer. The cyclic oligomer mixtures are generally liquid at temperatures above 300° C. and most often at temperatures above 225° C.

The mixtures useful in this invention contain very low proportions of linear oligomers. In general, no more than about 10% by weight, and most often no more than about 5%, of such linear oligomers are present. The mixtures also contain low percentages (frequently less than 30% and preferably no higher than about 20%) of polymers (linear or cyclic) having a degree of polymerization greater than about 30. Such polymers are frequently identified hereinafter as "high polymer". These properties coupled with the relatively low melting points and viscosities of the cyclic oligomer mixtures, contribute to their utility.

These mixtures can be prepared by a condensation reaction involving bishaloformates of the dihydric phenols of Formulae III and IV of formula

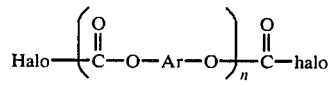

V.

wherein O—Ar—O is the reaction residue of either of the Formula III or IV dihydric phenols which have been reacted with phosgene or the bromo analogue, halo is chloro or bromo and n is an integer of one to about six. Usually no more than one of the O—Ar—O residues is derived from a Formula III dihydric phenol; however there can be two or more.

The cyclic oligomer forming reaction typically takes place interfacially when a solution of said bishaloformate in a substantially non-polar organic liquid is contacted with a tertiary amine from a specific class and an aqueous alkali metal hydroxide solution.

In one method for preparing the cyclic oligomer mixture, at least one such bishaloformate is contacted with at least one oleophilic aliphatic or heterocyclic tertiary amine and an aqueous alkali metal hydroxide solution having a concentration of about 0.1–10M, said contact being effected under conditions resulting in high dilution of bishaloformate, or the equivalent thereof, in a substantially non-polar organic liquid which forms a two-phase system with water; and subsequently, the resulting cyclic oligomer mixture is separated from at least a portion of the high polymer and insoluble material present.

The tertiary amines useful in the preparation of the cyclic polycarbonate oligomers generally comprise those which are oleophilic (i.e., which are soluble in and highly active in organic media) and more particularly those which are useful for the formation of polycarbonates. Reference is made, for example, to the tertiary amines disclosed in the aforementioned U.S. Pat. Nos. 4,217,438 and in 4,368,315, the disclosure of which is also incorporated by reference herein. They include aliphatic amines such as triethylamine, tri-n-propylamine, diethyl-n-propylamine and tri-n-butylamine and highly nucleophilic heterocyclic amines such as 4-dimethylaminopyridine (which, for the purposes of this invention, contains only one active amine group). The preferred amines are those which dissolve preferentially in the organic phase of the reaction system; that is, for which the organic-aqueous partition coefficient is greater than 1. This is true because intimate contact between the amine and bischloroformate is essential for the formation of the cyclic oligomer mixture. For the most part, such amines contain at least about 6 and preferably about 6–14 carbon atoms.

The most useful amines are trialkylamines containing no branching on the carbon atoms in the 1- and 2-positions. Especially preferred are tri-n-alkylamines in which the alkyl groups contain up to about 4 carbon atoms. Triethylamine is most preferred by reason of its particular availability, low cost, and effectiveness in the preparation of products containing low percentages of linear oligomers and high polymers.

The aqueous alkali metal hydroxide solution is most often lithium, sodium or potassium hydroxide, with sodium hydroxide being preferred because of its availability and relatively low cost. The concentration of said solution is about 0.2–10M and preferably no higher than about 3–5M.

The fourth component in the cyclic oligomer preparation method is a substantially non-polar organic liquid which forms a two-phase system with water. The identity of the liquid is not critical, provided it possesses the stated properties. Illustrative liquids are aromatic hydrocarbons such as toluene and xylene; substituted aromatic hydrocarbons such as chlorobenzene, o-dichlorobenzene and nitrobenzene; chlorinated aliphatic hydrocarbons such as chloroform and methylene chloride; and mixtures of the foregoing with ethers such as tetrahydrofuran.

To prepare the cyclic oligomer mixture according to the above-described method, the reagents and components are maintained in contact under conditions wherein the bischloroformate is present in high dilution, or equivalent conditions. Actual high dilution conditions, requiring a large proportion of organic liquid, may be employed but are usually not preferred for cost and convenience reasons. Instead, simulated high dilution conditions known to those skilled in the art may be employed. For example, in one embodiment of the method the bischloroformate or a mixture thereof with the amine is added gradually to a mixture of the other materials. It is within the scope of this embodiment to incorporate the amine in the mixture to which the bischloroformate is added, or to add it gradually, either in admixture with the amine or separately. Continuous or incremental addition of the amine is frequently preferred, whereupon the cyclic oligomer mixture is obtained in relatively pure form and in high yield.

Although addition of the bischloroformate neat (i.e., without solvents) is within the scope of this embodiment, it is frequently inconvenient because many bischloroformates are solids. Therefore, it is preferably added as a solution in a portion of the organic liquid. The proportion of organic liquid used for this purpose is not critical; about 20–80% by weight, and especially about 40–60%, is prepared.

The reaction temperature is generally in the range of about 0°–50° C. It is most often about 0°–40° C. and preferably 20°–40° C.

For maximization of the yield and purity of cyclic oligomers as opposed to high polymer and insoluble and/or interactable by-products, it is preferred to use not more than about 0.7 mole of bischloroformate per liter of organic liquid present in the reaction system, including any liquid used to dissolve said bischloroformate. Preferably, about 0.003–0.6 mole of bischloroformate is used. It should be noted that this is not a molar concentration in the organic liquid when the bischloroformate is added gradually, since it is consumed as it is added to the reaction system.

The molar proportions of the reagents constitute another important feature for yield and purity maximization. The preferred molar ratio of amine to bischloroformate is about 0.1–1.0:1 and most often about 0.2–0.6:1. The preferred molar ratio of alkali metal hydroxide to bischloroformate is about 1.5–3:1 and most often about 2–3:1.

Step II of the cyclic oligomer preparation method is the separation of the oligomer mixture from at least a portion of the high polymer and insoluble material present. When other reagents are added to the alkali metal hydroxide and the preferred conditions and material proportions are otherwise employed, the cyclic oligomer mixture (obtained as a solution in the organic liquid) typically contains less than 30% by weight and frequently less than about 20% of high polymer and insoluble material. When all of the preferred conditions are employed, the product may contain 10% or even less of such material. Depending on the intended use of the cyclic oligomer mixture, the separation step may then be unnecessary.

Therefore, a highly preferred method for preparing the cyclic oligomer mixture comprises the single step of conducting the reaction using as the amine at least one aliphatic or heterocyclic tertiary amine which, under the reaction conditions, dissolves preferentially in the organic phase of the reaction system, and gradually adding bischloroformate, amine and alkali metal hydroxide simultaneously to a substantially non-polar organic liquid or a mixture of said liquid with water, said liquid or mixture being maintained at a temperature in the range of about 0°–50° C.; the amount of bischloroformate used being up to about 0.7 mole for each liter of said organic liquid present in the reaction system, and the molar proportions of amine and alkali metal hydroxide to bischloroformate being 0.2–1.0:1 and 2–3:1, respectively although greater quantities of amine or alkali hydroxide can be employed if desired; and recovering the cyclic oligomers thus formed.

As in the embodiment previously described, another portion of said liquid may serve as a solvent for the bischloroformate. Addition of each reagent is preferably continuous, but may be incremental for any or all of said reagents.

In preparation of oligomers some of the carbonate linkages can be replaced with ester linkages by use of ester containing bisphenol precursors such as the reaction product of greater than one mole of a bisphenol with one mole of a diacid chloride, such as terephthaloyl chloride and/or isophthaloyl chloride, in the formulation of the cyclic oligomers. In this manner aromatic copolyester carbonate oligomers, can be prepared wherein up to all but one of the carbonate units has been replaced by an aromatic carboxylic ester unit.

When a separation step is necessary, the unwanted impurities may be removed in the necessary amounts by conventional operations such as combining the solution with a non-solvent for said impurities. Illustrative non-solvents include ketones such as acetone and methyl isobutyl ketone and esters such as methyl acetate and ethyl acetate. Acetone is a particularly preferred nonsolvent. Recovery of the cyclic oligomers normally means merely separating the same from diluent (by known methods such as vacuum evaporation) and, optionally, from high polymer and other impurities.

With respect to the structure of the formulae, X is preferably alkylene of two to six carbon atoms, inclusive, alkylidene of one to six carbon atoms, inclusive, cyclalkylidene of six to twelve carbon atoms, inclusive, —S—, —O—, —S—S—,

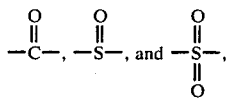

a is preferably 1.

R is preferably alkylene of two to four carbon atoms, inclusive or alkylidene of one to four carbon atoms, inclusive.

$R^1$ and $R^2$ are the same or different and are preferably alkyl of one to three carbon atoms, inclusive, chloro or bromo.

b and c are the same or different and are preferably 0, 1 or 2.

d and e are preferably 1.

$R_3$ and $R_4$ are the same or different and those alkyl without a $\beta$ hydrogen, e.g. methyl, phenyl, benzyl 2,2-dimethylpropyl are preferred. Most preferable are methyl and phenyl.

The cyclic oligomers are converted to linear polymers by standard melt reaction conditions utilizing transesterification type catalysts. Generally transesterifications are carried out in the melt state in general accordance with known processes described, inter alia, in *The Encyclopedia of Polymer Science*, Vols. 9 and 10 (1969); *Chemistry and Physics of Polycarbonates*, H. Schnell, Vol. 9, John Wiley and Sons, Inc. (1964); *Polycarbonates*, Christopher and Fox, Reinhold Corporation, (1962); U.S. Pat. Nos. 4,217,438; 4,329,443 and 4,217,438, all of which are hereby incorporated by reference.

The transesterification catalysts used in the preparation of the instant polycarbonate resins are any of the well known and conventional transesterification catalysts. These catalysts include the organic and inorganic bases, the organic and inorganic protic acids, and the Lewis acids. Some illustrative non-limiting examples of organic and inorganic base catalysts include sodium metal, lithium hydroxide, sodium carbonate, sodium acetate, sodium methylate, sodium borohydride, isopropylamine, pyridine, sodium benzoate, sodium phenoxide, sodium aluminumhydride, and sodium boronhydride. Some illustrative non-limiting examples of protic acid catalysts include hydrochloric acid, hydrofluoric acid, hydrobromic acid, sulfuric acid, sulfonic acid, methanesulfonic acid, benzene sulfonic acid, and phosphonic acid. Some illustrative non limiting examples of Lewis acid catalysts include borontrifluoride, stannic chloride, and dialkyl tin oxide. Other Lewis acid catalysts are disclosed, inter alia, in U.S. Pat. Nos. 4,045,464, 3,255,236, and 4,182,726, all of which are incorporated herein by reference. Other protic acid catalysts are disclosed, inter alia, in U.S. Pat. No. 3,767,648, which is incorporated herein by reference.

The amount of the catalyst employed is a catalytic amount. By catalytic amount is meant an amount effective to catalyze the reaction. Generally, molar ratios of catalyst to dihydric phenol in the range of from about $1 \times 10^{-5}$ to 1 to about $1 \times 10^{-1}$ to 1 can be used.

The crosslinking which occurs in the polycarbonates is generally physically manifested by the appearance of gels when the polycarbonate resin is placed in an organic solvent such as methylene chloride. The non-crosslinked polycarbonate will go into solution; the crosslinked polycarbonate will remain in gel form.

The crosslinked residue and useful articles made from this invention may optionally contain the commonly known and used additives such as, for example, antioxidants, mineral fillers, reinforcing agents, impact modifiers, colorants, ultraviolet radiation absorbers such as the benzophenones, benzotriazoles, and cyanoacrylates; color stabilizers such as the organophosphites described in U.S. Pat. Nos. 3,305,520 and 4,118,370, both of which are incorporated herein by reference; hydrolytic stabilizers such as the epoxides described in U.S. Pat. Nos. 3,489,716; 4,138,716 and 3,839,247, all of which are incorporated herein by reference, and flame retardants.

Some particularly useful reinforcing agents which may be used separately or in combination are carbon, aramid, glass and boron fibers and other reinforcements which may be chopped, woven, knit, braided, wound or shaped by any conventional method.

Some particularly useful flame retardants are the alkali and alkaline earth metal salts of organic sulfonic acids. These types of flame retardants are disclosed, inter alia, in U.S. Pat. Nos. 3,933,734; 3,938,851; 3,926,908; 3,919,167; 3,909,940; 3,853,396; 3,931,100; 3,978,024; 3,953,399; 3,917,599; 3,951,910 and 3,940,366, all of which are incorporated herein by reference.

The following are examples. These examples are intended to illustrate the embodiments within the inventive concept. The examples are not meant to narrow the inventive concept.

EXAMPLE 1

Preparation of a 2 Mole % Cyclic Oligomer Copolymer Utilizing Bis (4-Hydroxy-3-Methoxycarbonylphenyl) Methane with Bisphenol-A a. Preparation of bischloroformate oligomers. A 1000 ml. four neck flask was fitted with a mechanical stirrer, a pH probe, an aqueous caustic inlet tube and a Claisen adapter to which was attached a dry ice condenser and a gas inlet tube. To the flask was added 200 ml of methylene chloride, 200 ml. water, 1.26 g (0.004 mole) bis (4-hydroxy-3-methoxycarbonyl phenyl) methane and 44.7 g (0.196 mole) bisphenol-A. To the flask was then added phosgene at 2.0 g/min for 21 min. (42 g, 0.42 mole) with the pH maintained in the range 2 to 5 by addition of 25 wt. % aqueous sodium hydroxide. After completion of phosgene addition, the reaction mixture was stirred for an additional 15 min, and the methylene chloride layer was removed. The methylene chloride solution was used directly in the cyclization reaction.

b. Cyclization of the bischloroformate oligomers. A 1000 ml. flask was fitted with a mechanical stirrer and an addition funnel containing the bischloroformate oligomer solution prepared above. To the flask was added 80 g of 50% aqueous sodium hydroxide, 120 ml. water, 300 ml. methylene chloride and 6.4 ml. (0.046 mole) triethylamine. The bischloroformate oligomer solution was then added drop-wise over one hour to the slowly stirred reaction mixture. The reaction mixture was stirred an additional 15 minutes and then quenched with 3N aqueous HCL to pH of 3. The methylene chloride layer was removed, washed with 200 ml of 0.01M aqueous HCl, then washed with 200 ml of distilled water, dried over MgSO4, filtered and the solvent removed under vacuum to yield 42 g of a white solid. To that solid was then added 500 ml acetone. The resultant slurry was stirred for 30 minutes, then filtered and the solvent removed under vacuum to yield 24 g of the acetone-soluble cyclic oligomers, which were then used directly in the polymerization reaction.

c. Polymerization of the cyclic oligomers. To 6 g ($2.3 \times 10^{-2}$ mole) of the cyclic oligomers from above dissolved in 25 ml. methylene chloride was added 0.009 g ($2.3 \times 10^{-5}$ mole) tetramethylammonium tetraphenyl borate dispensed in 5 ml. methylene chloride. The solvent was then removed under vacuum and the resultant residue dried for 4 hours at 120° C. A 5 g sample of the mixture was then compression molded at 250° C. for 20 minutes into a 1.5 inch diameter disk.

A 2.0 g sample from the disk was then swelled in 40 ml methylene chloride and the resultant gel repeatedly soaked and washed with methylene chloride until no additional soluble resin was observed to be removed from the gel. The gel was then dried and weighed (0.81 g, 41% gel). The intrinsic viscosity of the soluble portion (methylene chloride, 25° C.) was 1.97 dl/g.

EXAMPLE 2

Preparation and Polymerization of a 4 Mole % Cyclic Oligomers Copolymer of Bis (4-Hydroxy-3-Methoxycarbonylphenyl)Methane with Bisphenol-A The same procedures as described above in Example 1 were used, starting with 2.53 g (0.008 mole) of bis (4-hydroxy-3-methoxycarbonylphenyl) methane and 43.8 g (0.192 mole) bisphenol-A.

The resultant resin exhibited 65% gels and an intrinsic viscosity of the soluble portion of 0.940 dl/g.

Preparation of Control Sample

A sample prepared essentially by the same procedure as above using bisphenol-A and no bis(4-hydroxy-3-methoxycarbonyl phenyl) methane exhibited 0.4% gels and intrinsic viscosity of 1.04 dl/g.

As is observed from the data, the incorporation of a branching agent within the cyclic oligomers brings about a cross-linked polycarbonate at the levels used as opposed to the standard linear polycarbonate. The amount of branching agent, that is the compound of Formula III, can vary widely and still obtain a non-linear system. At the lower percent branching agent, branched rather than cross-linked polycarbonates can occur. At the upper end of the range essentially all the incorporated agent produces cross-linked resin. The percentage of branching agent based on diphenol+branching agent is generally from about 0.1 to 10 mole percent and more specifically from about 0.5 to 5 mole percent of the diphenol plus branching agent.

What is claimed is:

1. A composition comprising at least one oligomer of the formula

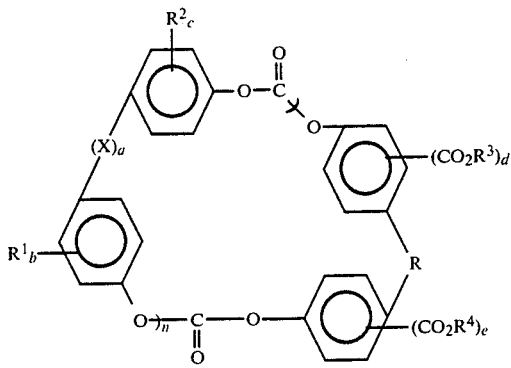

wherein
X is selected from the group consisting of alkylene of two to twelve carbon atoms, inclusive, alkylidene of one to twelve carbon atoms, inclusive, cycloalkylene of four to twelve carbon atoms, inclusive, cycloalkylidene of four to twelve carbon atoms, inclusive, —S—, —O—, —S—S—,

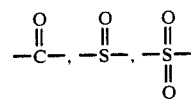

a is zero or 1;
n is an integer of one to about fifteen;
R is alkylene of two to eight carbon atoms, inclusive, or alkylidene of one to eight carbon atoms, inclusive;
$R^1$ and $R^2$ are the same or different and are alkyl or one to four carbon atoms, inclusive or halo;
b and c are the same or different and are an integers of zero to four; and
$R^3$ and $R^4$ are the same or different and are alkyl of one to eight carbon atoms, inclusive, or phenyl; and
d and e are individually integers of 0, 1 or 2 with the proviso that d+e is at least one.

2. The composition in accordance with claim 1 wherein X is alkylene of two to six carbon atoms, inclusive, alkylidene of one to six carbon atoms, inclusive, cycloalkylidene or six to twelve carbon atoms, inclusive, —S—, —O—, —S—S—,

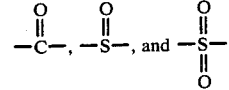

a is 1;
R is alkylidene of one to four carbon atoms, inclusive; or alkylene of two to four carbon atoms, inclusive;
$R^1$ and $R^2$ are the same or different and are alkyl of one to three carbon atoms, inclusive, chloro or bromo;
b and c are the same or different and are zero, 1 or 2;
$R^3$ and $R^4$ are alkyl having no β hydrogen or phenyl; and
d and e are both 1.

3. The composition in accordance with claim 2 wherein
X is isopropylidene;
a is 1;
b and c are each zero;
R is methylene;
$R^3$ and $R^4$ are methyl or phenyl and $CO_2R^3$ and $CO_2R^4$ are meta to R.

4. A composite material comprising a fibrous or matted material to which has been added or impregnated liquid cyclic oligomers of claim 1.

* * * * *